United States Patent [19]

Förster

[11] Patent Number: 4,600,382
[45] Date of Patent: Jul. 15, 1986

[54] ORTHODONTIC APPLIANCE

[75] Inventor: Rolf Förster, Pforzheim, Fed. Rep. of Germany

[73] Assignee: Bernhard Forster GmbH, Pforzheim, Fed. Rep. of Germany

[21] Appl. No.: 730,311

[22] Filed: May 2, 1985

[30] Foreign Application Priority Data

May 10, 1984 [DE] Fed. Rep. of Germany ....... 3417256

[51] Int. Cl.$^4$ .............................................. A60C 7/00
[52] U.S. Cl. ...................................................... 433/5
[58] Field of Search ............................................ 433/5

[56] References Cited

U.S. PATENT DOCUMENTS 862,881  8/1907  Case .......................................... 433/5
4,402,669  9/1983  Frazier ...................................... 433/5

Primary Examiner—Robert Peshock
Attorney, Agent, or Firm—Balogh, Osann, Kramer, Dvorak, Genova & Truab

[57] ABSTRACT

This invention relates to an orthodontic appliance comprising a low pull and/or a high pull, which low pull preferably extends through and is slidable in a guide sleeve of a nape pad, and the low pull and/or the high pull are provided at each end with a series of holes for a selective connection to spring elements connected to bow means. The novel orthodontic appliance is simpler, less bulky and less conspicuous. This is accomplished in that elastically stretchable flat strips of plastic material are provided at one end with an eyelet for connection to the low pull and/or the high pull at the series of holes and at the other end with an eyelet for connection to the bow means. That arrangement provides a pulling device which is flat rather than bulky and can easily be connected and which is convenient for the patient and can be made to have the color of the skin so that it is less conspicuous.

11 Claims, 7 Drawing Figures

ORTHODONTIC APPLIANCE

BACKGROUND OF THE INVENTION

1. Field of the Invention

This invention relates to an orthodontic appliance including a low pull and/or a high pull, which low pull preferably extends through and is slidable in a guide sleeve of a nape pad, and the low pull and/or the high pull are provided at each end with a series of holes for a selective connection to spring elements connected to bow means.

2. Description of the Prior Art

German Patent Specification No. 26 23 943 discloses such an orthodontic appliance comprising an extra-oral or outer face bow and a low pull for transmitting spring forces to an oral or inner correcting bow which is connected to molar teeth to be corrected. Spring elements are provided on both sides in the outer bow and in use extend beside and approximately parallel to the inner terminal portions of the inner bow and the spring elements are succeeded by the hooklike means for connection to the low pull, which extends through a guide sleeve and is in contact with a slideway in said sleeve. The low pull bears on a pad, which bears on the nape. The spring elements provided on both sides consist of tension springs and cooperate with scale-bearing housings so as to provide spring scales. A further development of that appliance is disclosed in the specification of German Pat. No. 26 48 989, which is a patent of addition to German Pat. No. 26 23 943.

In accordance with U.S. Pat. No. 4,353,691 a telescopically extensible hook connector for such orthodontic appliances includes a rubber cord for exerting a tensile force.

In the known orthodontic appliances the telescopic pulling means are inconvenient for the patient and are bulky, conspicuous and also expensive.

SUMMARY OF THE INVENTION

It is an object of the invention to provide an orthodontic appliance having pulling means which are simpler, less bulky and less conspicuous.

In a orthodontic appliance including a low pull and/or a high pull, which low pull preferably extends through and is slidable in a guide sleeve of a nape pad, and the low pull and/or the high pull are provided at each end with a series of holes for a selective connection to spring elements connected to bow means preferably including an extra-oral outer bow and an oral inner bow connected to the outer bow and adapted to be connected to the teeth to be corrected, that object is accomplished in that elastically stretchable flat strips of plastic material are provided at one end with an eyelet for connection to the low pull and/or the high pull at the series of holes and at the other end with an eyelet for connection to the bow means. That arrangement provides a pulling device, which is flat rather than bulky and can easily be connected and which is convenient for the patient and can be made to have the color of the skin so that it is less conspicuous.

The eyelet at one end of the flat strip of plastic material may be connected to the low or high pull at the associated series of holes by means of a double-headed pin, which is adapted to be inserted through the eyelet and any hole of the series, or by a double hook.

DETAILED DESCRIPTION OF THE PREFERRED EMBODIMENTS

Figure 1:
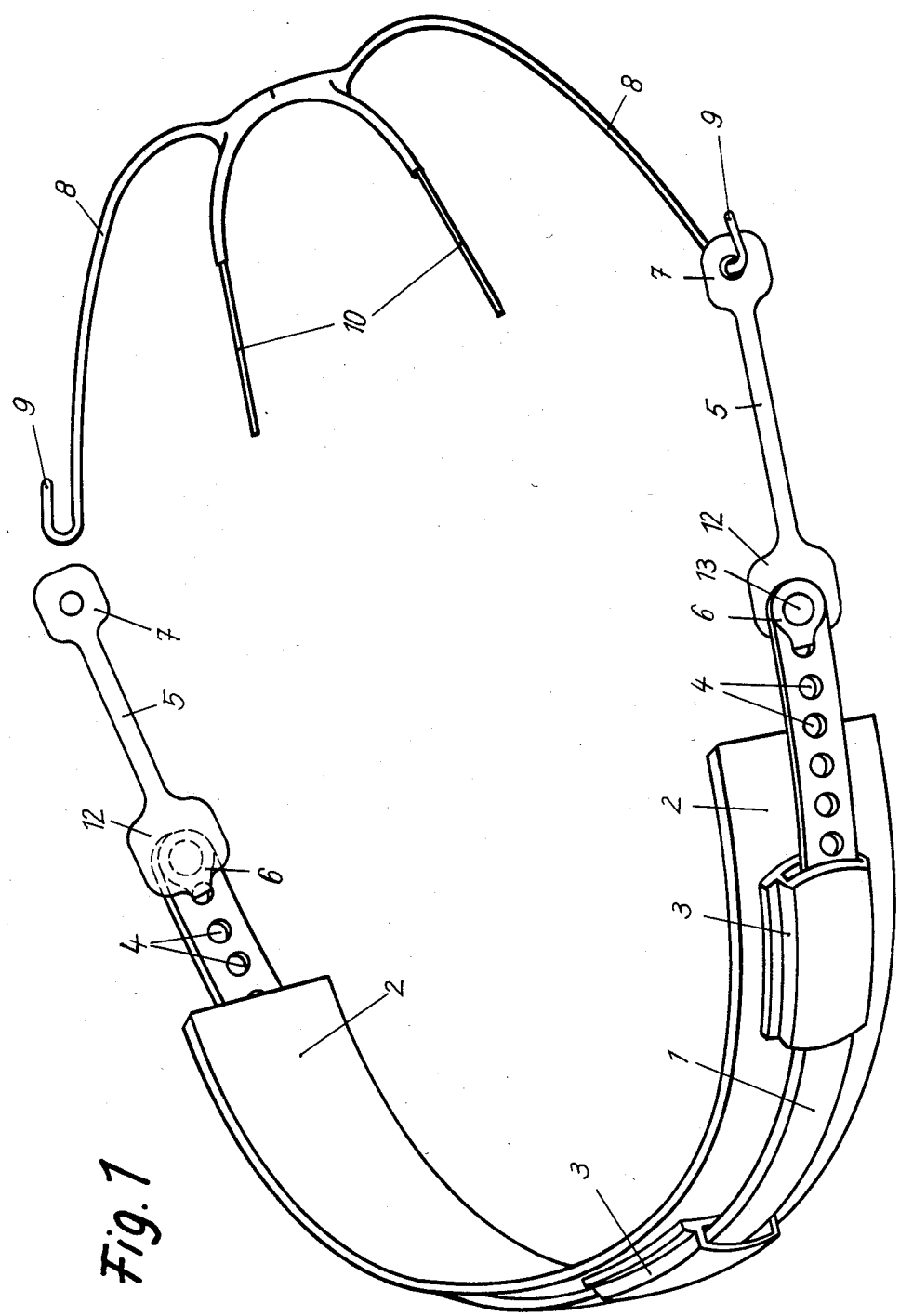
FIG. 1 is an elevation showing a low pull, elastically stretchable, flat strips of plastic, and outer an inner bows connected to said straps.

Further details of the orthodontic appliance in accordance with the invention will now be explained with reference to the drawing showing preferred embodiments.

FIG. 1 shows a low pull 1, which is provided with a fabric pad 2, which is adapted to be applied to the nape of the patient's neck. The low pull 1 extends through and is slidable in plastic guide sleeves 3. The low pull has opposite terminal portions, each of which is formed with a series of holes 4, to which elastically stretchable, flat pulling strips 5 of plastic are adapted to be selectively connected. Each of the pulling strips 5 is provided at opposite ends with eyelets 6 and 7, respectively. Each pulling strip 5 is selectively connected at one end by the eyelet 6 to one of the holes 4 and is connected at the other end by the eyelet 7 and a hook 9 to the outer bow 8, which carries the inner bow 10 for connection to teeth to be corrected.

In the embodiment shown in FIG. 1 the elastically stretchable flat strip 5 of plastic has been connected to the low pull 1 in that the strip 5 has been inserted through one of the holes 4 and has been reversely bent at that hole 4 and connected to another hole 4, by means of the eyelet 6. Adjacent to the low pull 1 the elastic strip 5 has a portion 12 which is enlarged in width and is intended to be applied to the face of the wearer. As the end portion of the strip 5 is inserted through the hole 4, the enlarged portion 12 is deformed to have a convex surface facing the face of the wearer so that that convex surface is in sliding contact with the face of the wearer.

Figure 2:
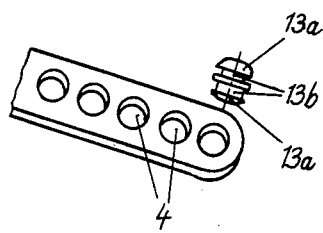
FIGS. 2 to 4 are elevations showing how an elastic strip is connected to one of a series of holes provided at one end of a low pull.
Figure 3:
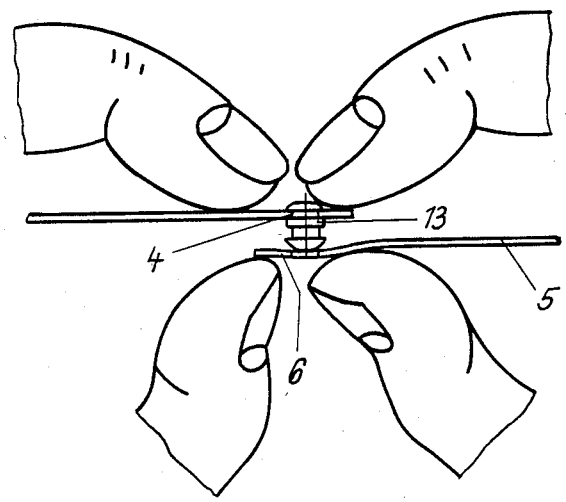
Figure 4:
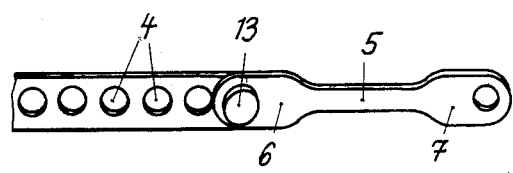

The eyelet 6 may be connected to the low pull 1 by means of a double-headed pin 13, as is shown in FIGS. 2 and 4, where the eyelet 6 and the selected hole 4 are in register. The pin 13 is provided at each end with a flat head 13a and its shank is formed with annular grooves 13b, which differ in diameter and fit the eyelet 6 and the hole 4 disposed between the heads 13a.

Figure 5:
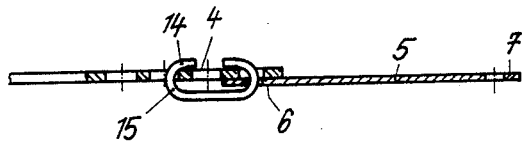
FIG. 5 is a sectional view showing other means for connecting an elastic strip to one of said series of holes.

In the embodiment shown in FIG. 5 the eyelet 6 and the selected hole 5 are connected by means of a double-hooked member 14, which is similar to a chain link and which may be enlarged in width at 15 on the side facing the face of the wearer for improved sliding contact.

Figure 6:
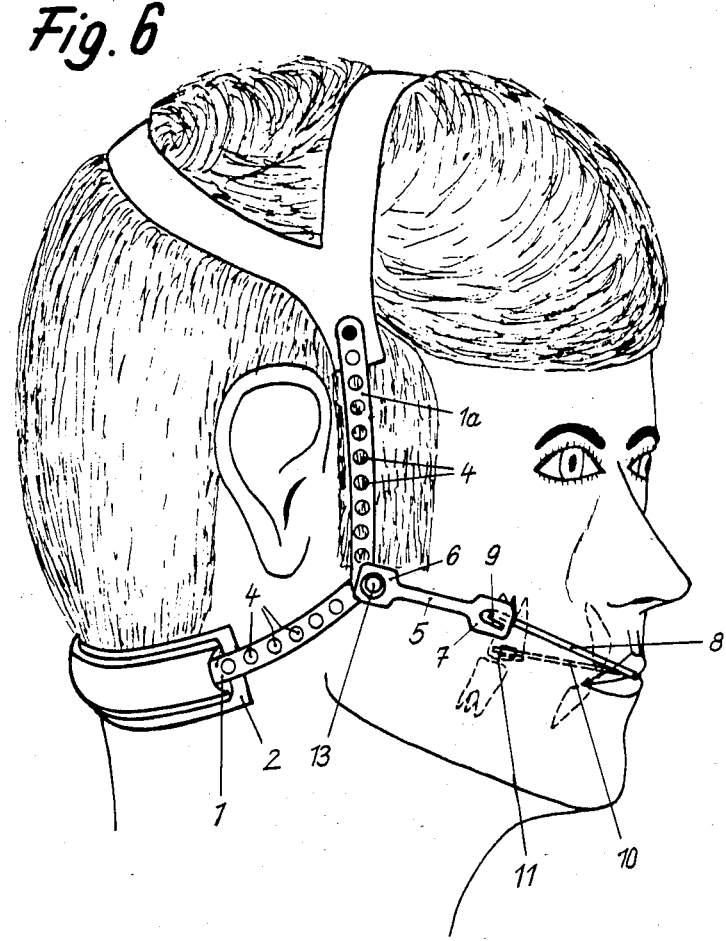
FIG. 6 shows an orthodontic appliance comprising a low pull, a high pull, an elastic strip of plastic, an outer bow and an inner bow.

FIG. 6 shows an orthodontic appliance comprising a low pull 1, a high pull 1a, a pulling strap 5, an outer bow 8 and a tooth-correcting inner bow 10 connected at 11 to a tooth to be corrected. The eyelet 6 and a hole 4 are connected by a double-headed pin 13. The outer bow 8 is provided at each end with a hook 9 connected to an eyelet 7.

Figure 7:
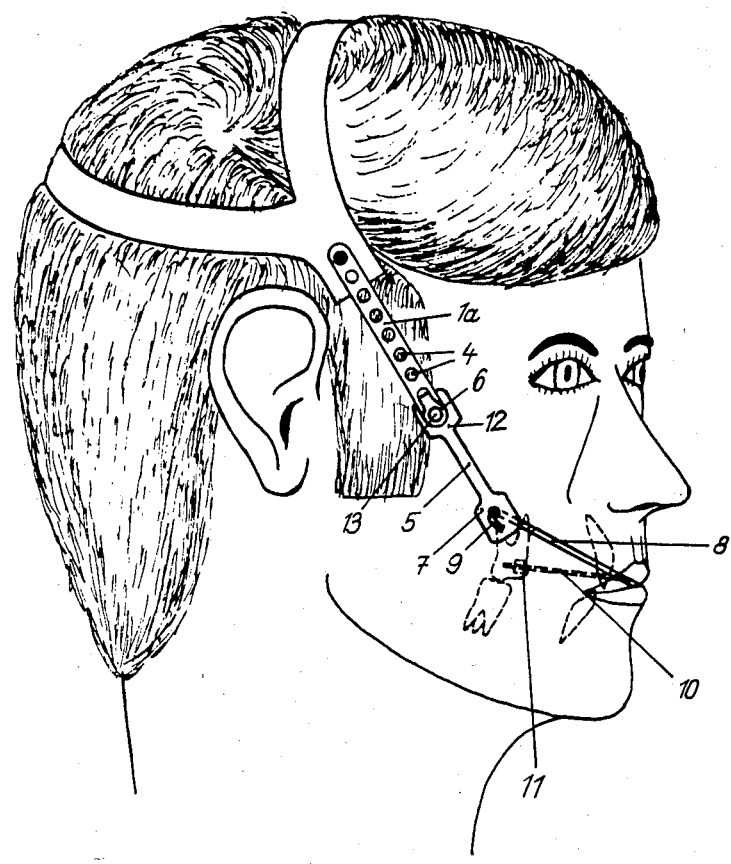
FIG. 7 shows an orthodontic appliance comprising a high pull connected by a plastic pulling strip to outer and inner bows.

FIG. 7 shows a similar orthodontic appliance in which the low pull 1 of FIG. 6 has been omitted. Alternatively, the high pull 1a may be omitted so that the appliance is held only by means of a slidable low pull 1. This will depend on the tension vector required for the desired tooth correction.

The holes 4 provided in the low pull 1 or the high pull 1a may be arranged in parallel rows of staggered holes so that the tensile force can be adjusted in smaller increments. Such an arrangement is not shown here.

I claim:

1. In an orthodontic appliance comprising bow means adapted to be connected to at least one tooth to be corrected and having opposite outer end portions adapted to be disposed on respective sides of a head of a wearer, retaining strap means having one pair of terminal portions adapted to be disposed on opposite sides of the head of the wearer at a distance from respective ones of said end portions, each of said terminal portions being formed with at least one series of holes spaced apart along said terminal portion, and two resilient elements, each of which is detachably connected to one of said terminal portions at one of said holes therein and to one of said end portions and is adapted to be stretched to pull said one end portion toward said one hole, the improvement comprising each of said resilient elements comprises an elastically stretchable flat plastic strip, which is provided at one end with a first eyelet detachably connected to one of said end portions and is provided at its other end with a second eyelet detachably connected to one of said terminal portions at one of said holes therein, each of said flat strips extending near the second eyelet thereof through one of said holes and having near the associated terminal portion a portion which is enlarged in width and adapted to contact the face of the wearer, said enlarged portion having a convex surface facing the face of the wearer, so that the convex surface is in sliding contact with the face of the wearer, when said flat strips extend through said respective ones of said holes.

2. The improvement set forth in claim 1 as applied to an orthodontic appliance in which said retaining strap means comprise a low pull provided with said terminal portions.

3. The improvement set forth in claim 2 as applied to an orthodontic appliance comprising a pad adapted to be applied to the nape of the neck of the wearer and provided with at least one guide sleeve, said low pull extending through said guide sleeve and being slidable along the same.

4. The improvement set forth in claim 1 as applied to an orthodontic appliance in which said retaining strap means comprise a high pull adapted to be applied around the head of the wearer and provided with said terminal portions.

5. The improvement set forth in claim 1 as applied to an orthodontic appliance in which said retaining strap means comprise a low pull adapted to be applied to the nape of the neck of the wearer and a high pull adapted to be applied to the head of the wearer.

6. The improvement set forth in claim 1 as applied to an orthodontic appliance in which each of said low pull and said high pull comprises one pair of said terminal portions, wherein said second eyelet of each of said flat plastic strips is detachably connected to one terminal portion of each of said pairs.

7. The improvement set forth in claim 1, wherein two double-headed pins are provided, each of which extends through said second eyelet of one of said flat strips and through one of said holes of the associated terminal portion.

8. The improvement set forth in claim 7, wherein each of said pins comprises a shank, which is provided with a flat head at each of its ends and is formed with two axially spaced apart annular grooves fitting said second eyelet and said one hole, respectively.

9. The improvement set forth in claim 1, wherein two connecting members are provided, each of which has a first hook-shaped end portion extending through said second eyelet of one of said flat strips and a second hook-shaped end portion extending through one said holes of the associated terminal portion.

10. The improvement set forth in claim 1, wherein each of said flat strips is reversely bent at said one hole.

11. The improvement set forth in claim 1, wherein each of said terminal portions is formed with two series of staggered holes.

* * * * *